United States Patent [19]

Seamon et al.

[11] Patent Number: 5,350,864

[45] Date of Patent: Sep. 27, 1994

[54] AMINOALKYLCARBAMYL DERIVATIVES OF FORSKOLIN AS INTERMEDIATES FOR THE SYNTHESIS OF USEFUL FORSKOLIN DERIVATIVES

[75] Inventors: Kenneth B. Seamon, Silver Spring; Joan Robbins, Chevy Chase; Antonio Laurenza, Bethesda, all of Md.

[73] Assignee: The United States of America as represented by the Department of Health and Human Services, Washington, D.C.

[21] Appl. No.: 518,719

[22] Filed: May 3, 1990

[51] Int. Cl.$^5$ ............................................. C07D 311/92
[52] U.S. Cl. .................................................... 549/389
[58] Field of Search ................................ 549/389, 223

[56] References Cited

U.S. PATENT DOCUMENTS 4,920,146  4/1990  Kosley, Jr. et al. ................. 514/437

FOREIGN PATENT DOCUMENTS 8805047  7/1988  PCT Int'l Appl. .

*Primary Examiner*—Nicky Chan
*Attorney, Agent, or Firm*—Morgan & Finnegan

[57] ABSTRACT

The subject matter of the present invention relates to aminoalkylcarbamates of forskolin and the methods of using these compounds. Specifically, the aminoalkylcarbamates may be utilized in the synthesis of forskolin derivatives. The final derivatives may, in turn, be used in the development of in vivo and in vitro assays designed to study different proteins.

5 Claims, 6 Drawing Sheets a. CDI/CH$_2$Cl$_2$/4hrs., b. EDA/CH$_2$Cl$_2$/12hrs., c. AcOH/MeOH/12hrs.
d. CDI/TEA/CH$_2$Cl$_2$/12hrs., e. EDA/CH$_2$Cl$_2$/12hrs., f. FMOC/TEA/CH$_2$Cl$_2$/5hrs., 0°C
g. (Ac)$_2$O/Pyridine/CH$_2$Cl$_2$/12hrs., h. AcOH/MeOH/12hrs., i. Piperidine/CH$_2$Cl$_2$/1 hr.

AMINOALKYLCARBAMYL DERIVATIVES OF FORSKOLIN AS INTERMEDIATES FOR THE SYNTHESIS OF USEFUL FORSKOLIN DERIVATIVES

BACKGROUND OF THE INVENTION

1. Technical Field

The subject matter of the present invention relates to aminoalkylcarbamates of forskolin and the uses of these compounds. Specifically, the aminoalkylcarbamates may be utilized as intermediates in the synthesis of forskolin derivatives. The final derivatives or analogs may, in turn, be used in the development of in vivo and in vitro assays designed to study different proteins.

2. Background Information

Forskolin is a diterpene which can interact with a diverse group of membrane proteins including adenylate cyclase and the glucose transporter (Laurenza et al., *Trends in Pharmacological Sciences* 10:442 (1989)). Forskolin is a natural product and was originally isolated from methanol extracts derived from the roots of Coleus Forskohlii found on the indian subcontinent (Bhat et al., *Tetrahedron Letters* 19:1669 (1977)). Other diterpenes similar in structure to forskolin were isolated from the same methanol extracts including 1,9-dideoxyforskolin, 7-desacetylforskolin, 6-acetyl-7-desacetylforskolin and 9-deoxyforskolin.

Forskolin produces marked cardiotonic effects due to its ability to activate the enzyme adenylate cyclase and increase intracellular cyclic AMP (Metzger et al., *Arzneim, Forsch.* 31:1248 (1981)). The ability of forskolin to interact directly with adenylate cyclase is a unique property of this diterpene, and forskolin consequently has been used extensively by biomedical researchers (Seamon et al., *Adv. in Cyclic Nucl. Res.* 20:1–150 (1988)). The ability of forskolin to increase cyclic AMP in vivo has prompted many investigations into the therapeutic potential of forskolin to treat a number of indications including asthma, glaucoma and heart disease (Burka, *Can. J. Physiol. Pharmacol.* 61:681 (1983)), Caprioli et al., *Invest. Opthamol. Vis. Sci.* 25:268 (1984) and Briston et al., *J. Clin. Invest.* 74:212 (1984)).

Since forskolin is a natural product, there have been a number of investigations into the total synthesis of the diterpene. Many research groups have actively pursued different methods in developing the complete synthesis of forskolin and have utilized an Intramolecular Diels Alder construction for synthesizing key intermediates (Jenkins et al., *J.C.S. Chem. Commun.* p. 1423 (1984), Nicolaou et al., *J.C.S. Chem. Commun.* p. 421 (1984) and Ziegler et al., *Tetra. Letters* 25:3307 (1985)). Several groups have succeeded in the total synthesis of forskolin (Ziegler et al., *J. Am. Chem. Soc.* 109:8115 (1987), Hashimoto et al., *J. Am. Chem. Soc.* 110:3670 (1988) and Corey et al., *J. Am. Chem. Soc.* 110:3672 (1988)).

Currently, there is a great deal of interest in semi-synthetic analogs or derivatives of forskolin. The importance of the α-face of the molecule was defined by the inability of 1,9-dideoxyforskolin and derivatives of forskolin, with the 1- and 9-hydroxyl groups modified, to activate adenylate cyclase. (Bhat et al., *J. Med. Chem.* 26:486 (1983) and Seamon et al., *J. Med. Chem.* 26:486 (1983)).

Other derivatives of forskolin have been synthesized and tested for their ability to activate adenylate cyclase. These derivatives include ester analogs of forskolin with different acyl groups esterified at the 1α-, 6β-, and 7β-hydroxyl groups (Bhat et al., *J. Med. Chem.* 26:486 (1983)). Water soluble derivatives of forskolin have also been synthesized (Khandelwal et al., *J. Med. Chem.* 31:1872 (1988) and Laurenza et al., *Mol. Pharmacol* 33:133 (1987)). Procedures have been developed for the selective acylation of the 1-, 6-, or 7-hydroxyl groups via the specific protection of the 1-hydroxyl group with dimethylformamide acetal (Kosley et al., *J. Org. Chem.* 54:2972 (1989)). A method has also been developed to produce 6- and 7-carbamate derivatives of forskolin containing different groups attached to forskolin through a stable carbamate linkage (O'Malley et al., *J. Org. Chem.* 55:1102 (1990)). 7-Carbamate derivatives are produced by the nucleophilic attack of primary or secondary amines on a 7-acyl imidazolium intermediate of forskolin. 6-Carbamates are produced by the regioselective attack of primary and secondary amines on the 6,7-carbonate of forskolin.

Derivatives of forskolin have been synthesized and tested for their ability to activate adenylate cyclase. Initial studies demonstrated the importance of the 1- and 9-hydroxyl groups of forskolin for the activation of adenylate cyclase (Seamon et al., *J. Med. Chem.* 26:486 (1983)). Other derivatives of forskolin have been described that are active at adenylate cyclase (Seamon et al., *J. Med. Chem.* 26:486 (1983)). These include 7-acyl derivatives of forskolin that contain short alkyl chains such as 7-desacetyl-7-propionylforskolin (Seamon et al., *J. Med. Chem.* 26:486 (1983)). Other derivatives that can activate adenylate cyclase but are less potent than forskolin include 14,15-dihydroforskolin, 11β-hydroxyforskolin, 6-acetyl-7-desacetylforskolin, and 7-desacetylforskolin (Seamon et al., *J. Med. Chem.* 26:486 (1983)).

Other derivatives of forskolin do not activate or are not potent at activating adenylate cyclase. 1,9-Dideoxyforskolin does not activate adenylate cyclase, and derivatives of forskolin, where the 1- and 9-hydroxyl groups are conjugated, are inactive at adenylate cyclase (Seamon et al., *J. Med. Chem.* 26:486 (1983)). 7-Acyl derivatives of forskolin that contain lipophilic groups are not potent at activating adenylate cyclase (Seamon et al., *J. Med. Chem.* 26:486 (1983)).

As mentioned above, water soluble derivatives of forskolin have been synthesized. These include 7-acyl derivatives that contain heterocyclic rings which were almost as potent at adenylate cyclase as forskolin. Water soluble derivatives of forskolin that contain heterocyclic amino acids esterified at the 6-hydroxyl group are equipotent with forskolin (Khandelwal et al., *J. Med. Chem.* 31:1872 (1988) and Laurenza et al., *Mol. Pharmacol.* 32:133 (1987)).

Derivatives of forskolin have been synthesized and used for biochemical studies. These include α-haloacetyl derivatives of forskolin such as 7-descacetyl-7-bromoacetylforskolin and 7-desacetyl-7-chloroacetylforskolin which have been used to block the forskolin binding site on adenylate cyclase (Laurenza et al., *Mol. Pharmacol.* 37:69 (1990)). 7-Desacetyl-7-hemisuccinylforskolin has been synthesized and coupled to solid supports (Pfeuffer et al., *Proc. Natl. Acad. Sci. USA* 83:3086 (1985), Pfeuffer et al., *EMBO J.* 4:3675 (1985) and Smigel et al., *J. Biol. Chem.* 201:1976 (1988)). These supports have been used for the isolation and purification of adenylate cyclase. 7-Desacetyl-7-hemisuccinylforskolin has also been used as an intermediate for the synthesis of iodinated photoactivatable derivatives of forskolin for covalently labelling adenylate cyclase (Pfeuffer et al., *FEBS Lett.* 248:13 (1989)).

The synthesis of forskolin analogs has been aimed predominantly at designing those derivatives of forskolin that would be active at adenylate cyclase. There is much less information available concerning the interaction of forskolin at other forskolin binding proteins. Forskolin interacts with proteins other than adenylate cyclase, and there is some information regarding the binding of forskolin and forskolin analogs at the glucose transporter. 1,9-Dideoxyforskolin and derivatives of forskolin that contain lipophilic groups esterified at the 7-hydroxyl group inhibit glucose transport in adipocyte membranes (Joost et al., *Mol. Pharmacol.* 33:449 (1988)). These derivatives are not active at adenylate cyclase.

7-Desacetyl-7-hemisuccinylforskolin has been used as a starting material to synthesize photoactivatable derivatives of forskolin containing radioactive iodine (Wadzinski et al., *J. Biol. Chem.* 262:5978 (1978)). These derivatives have been used to covalently label the glucose transporter in a variety of tissues.

Forskolin and derivatives of forskolin could be used for a number of purposes due to the ability of forskolin to interact with a number of diverse and physiologically important proteins (Laurenza et al., *Trends in Pharmacol. Sci.* 10:442 (1989)). However, the derivatives of forskolin that have been synthesized to date have not been designed to be specific for the different sites of action of forskolin. For example, forskolin is equipotent at activating adenylate cyclase and inhibiting glucose transport. There has not been any rationale in designing derivatives of forskolin that would be potent at adenylate cyclase and not potent at the glucose transporter.

Many of the derivatives of forskolin that have been developed have been ester analogs. These include the α-haloacetyl analogs of forskolin, 7-bromoacetyl-7-desacetylforskolin and 7-chloracetyl-7-desacetylforskolin and derivatives utilizing 7-desacetyl-7-hemisuccinylforskoklin as an intermediate. There are potential problems in using ester-analogs for in vivo and in vitro studies. For example, ester analogs of forskolin are susceptible to hydrolysis and rearrangement under mildly basic conditions (Bhat et al., *J. Chem. Soc. Perkins Trans.* 1, p. 767 (1982)).

It would be desirable to have analogs of forskolin that would be stable and specific for forskolin binding proteins. The synthesis of such analogs could best be achieved by the use of specific intermediates that would have the following properties: 1) stability; 2) chemical groups that would be reactive so that they could be modified to produce a number of different final derivatives; and 3) reactive groups placed at positions on forskolin such that they would produce final derivatives that were specific for different forskolin binding proteins.

All patents and publications referred to herein are hereby incorporated by reference.

SUMMARY OF THE INVENTION

The present invention relates to aminoalkylcarbamates of forskolin and methods for utilizing these compounds. More specifically, the aminoalkylcarbamates of the invention may serve as intermediates in the formation of useful forskolin derivatives.

Four such aminoalkylcarbamate intermediates of forskolin which may be utilized in the synthesis of forskolin derivatives include the 6-aminoethylcarbamate, 7-aminoethylcarbamate, 1-aminoethylcarbamate, and 9-aminoethylcarbamate of forskolin.

In order to synthesize a final derivative from aminoethylcarbamate, an activated ester is added to the intermediate which has been dissolved in an organic solvent. After a suitable period of time, formation of the derivative of interest will occur. The activated ester chosen may be, for example, N-hydroxysuccinimide.

6,7-Disubstituted carbamates may also be synthesized by reacting 1,9-dimethylformamide-7-desacetylforskolin with carbonyldiimidazole in the presence of triethylamine. The 6,7-carbonate is formed and then reacted with a primary or secondary amine to form the 6-carbamate. The 6-aminoalkylcarbamate is then protected with fluorenylmethoxychloroformate. The protected amine is then reacted with carbonyldiimidazole to form the acylimidazolium derivative. This derivative is reacted with a primary or secondary amine to form the 6,7-dicarbamate of forskolin.

The present invention also includes a method of measuring the P-glycoprotein in a tissue sample. Specifically, a radioactive derivative of 6-aminoalkylcarbamyl-1,9-dideoxyforskolin is synthesized, and this compound is then added to membranes extracted from biopsy samples taken from tumors. The amount of radioactive derivative that is bound to the tissue sample is then measured, using a filtration assay to separate the bound from free ligand.

Additionally, the present invention includes a method of visualizing forskolin binding proteins in tissue samples wherein, first, a fluorescent derivative of forskolin is synthesized by reacting an aminoalkylcarbamate of forskolin with an activated ester or an isothiocyanate of a fluorescent molecule. The derivative is then added to tissue samples mounted on slides, and the slides are then examined under fluorescence microscopy to visualize the forskolin binding proteins.

Furthermore, the present invention also includes a method for measuring the amount of a forskolin binding protein in cells, using cell sorting. A fluorescent derivative of forswkolin is synthesized by reacting an aminoalkylcarbamate of forskolin with an activated ester or an isothiocyanate of a fluorescent molecule. The derivative is then added to cells, and the cells are then analyzed by cell sorters in order to determine the amount of cells that bind the fluorescent derivative.

Moreover, the present invention also encompasses a method of screening for drugs that bind to forskolin binding proteins. A derivative of an aminoalkylcarbamate of forskolin is reacted with a reactive derivative of biotin in order to produce a biotin conjugated forskolin derivative. This biotin conjugated forskolin derivative is then added to a test sample, and the biotin conjugated forskolin derivative that is bound to the test sample is separated from the free biotin conjugated forskolin derivative. The bound biotin conjugated forskolin derivative is then quantitated by adding avidin which has been conjugated with a suitable detection system.

Derivatives of the present invention have different specificity for different forskolin binding proteins. Furthermore, the derivative may be coupled to a solid support, for purification of adenylate cyclase or the glucose transporter depending on the derivative of use. The derivative may also bind to tissues with a high affinity, or be utilized for a therapeutic purpose. Additionally, the derivative may be administered with a chemotherapeutic agent in order to cause a sensitization to the agent. The derivative may also be used to block glucose uptake, measure the level of glucose transporter protein in tissues, or for the purpose of histopathological analysis with respect to tissue samples. An iodinated derivative or a fluorinated derivative may be used for the in vivo imaging of forskolin binding proteins using SPEC scanning or PET scanning. Moreover, the derivative may be used to screen for therapeutic agents, and may also be coupled to a carrier protein.

DETAILED DESCRIPTION OF THE INVENTION

The present invention relates to aminoalkylcarbamates of forskolin which may be utilized as intermediates in the preparation of derivatives of forskolin which serve therapeutic or diagnostic purposes. Additionally, the invention relates to methods of utilizing the aminoalkylcarbamate compounds.

Figure 1:
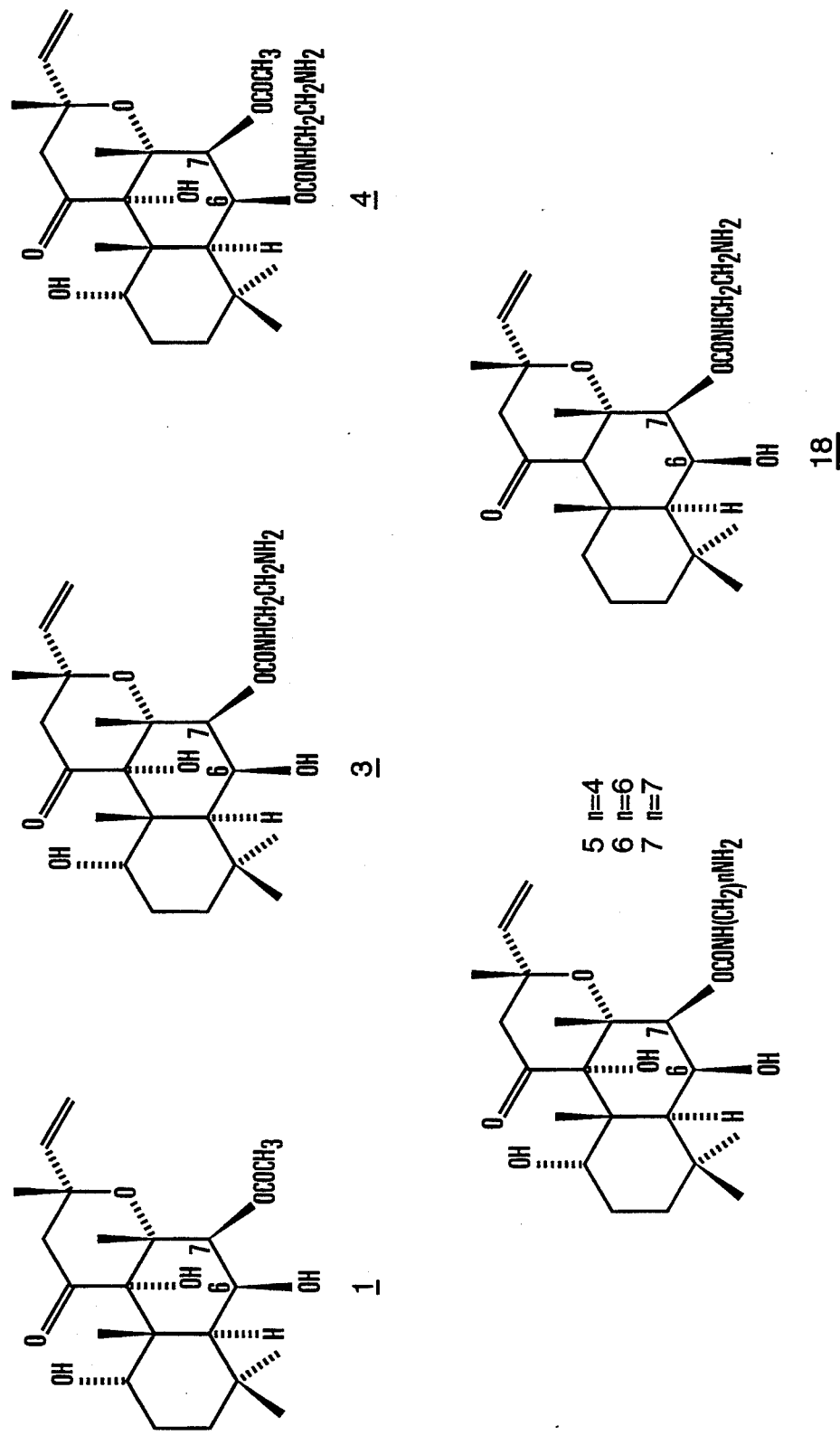
FIG. 1 shows the structures of forskolin (compound 1) and the following amino-alkyl-carbamate intermediates of forskolin: 7-aminoethyl-carbamylforskolin (compound 3), 6-aminoethylcarbamylforskolin (compound 4), 7-aminobutylcarbamylforskolin (compound 5), 7-aminohexylcarbamylforskolin (compound 6), 7-aminoheptylcarbamylforskolin (compound 7), and 7-aminoethylcarbamyl-1,9-dideoxyforskolin (compound 18)

The numbers of the compounds utilized below refer to structures of the aminoalkylcarbamate intermediates shown in FIG. 1, structures in the synthetic scheme shown in FIG. 2 or the structures of the derivatives shown in FIG. 3.

Carbamates are intrinsically more stable to hydrolysis than esters and are resistant to esterases. Primary amino groups are very reactive and react quite rapidly with activated esters such as N-hydroxysuccinimide activated esters to form amides and with isothiocyanates to form stable thioureas. Therefore, aminoalkylcarbamates of forskolin are quite useful as the compounds are stable, and contain reactive groups. Furthermore, the reactive groups can be synthesized at different positions on forskolin to produce intermediates with different specificities for different forskolin binding proteins.

Forskolin contains four positions where carbamates can be synthesized. These are the 1α-and 9α-hydroxyl groups and the 6β-hydroxyl and 7β-acetoxy group.

Such carbamates of forkolin, which can be utilized as intermediates in the synthesis of forskolin derivatives, have the formula:

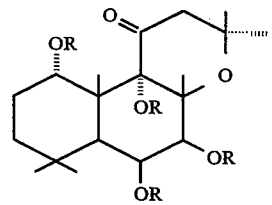

wherein R is CONH(R$_1$)NH$_2$, R$_1$ is a hydrocarbon group of the formula (CH$_2$)$_n$ or CH$_2$CH=CH(CH$_2$)$_n$, and wherein n=1, 2, 4, 5, or 7.

Previous studies have demonstrated that derivatives of forskolin with heterocyclic amino acids esterified at the 6β-hydroxyl groups are very potent at activating adenylate cyclase (Laurenza et al., Mol. Pharm. 32:133 (1987)). Therefore, 6-aminoalkylcarbamates of forskolin were used in the present invention as intermediates to form forskolin derivatives with specificity for adenylate cyclase.

The 6-aminoalkylcarbamate suitable for use in the methods to which this invention relates has the formula:

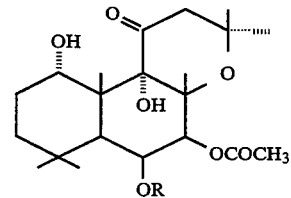

wherein R is CONH(R$_1$)NH$_2$, R$_1$ is a hydrocarbon group of the formula (CH$_2$)$_n$ or CH$_2$CH=CH(CH$_2$)$_n$ and n=1, 2, 4, 5 or 7.

Forskolin derivatives with lipophilic groups esterified at the 7β-hydroxyl group of forskolin are potent at the glucose transporter. Therefore, 7-aminoalkylcarbamates of forskolin were also synthesized in the present invention. These intermediates can be used to synthesize derivatives with specificity for the glucose transporter.

The 7-aminoalkylcarbamate suitable for use in the methods to which this invention relates has the formula:

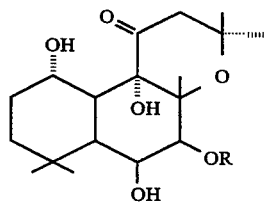

wherein R is CONH(R$_1$)NH$_2$, R$_1$ is a hydrocarbon group of the formula (CH$_2$)$_n$ or CH$_2$CH=CH(CH$_2$)$_n$ and n=1, 2, 4, 5 or 7.

Figure 2:
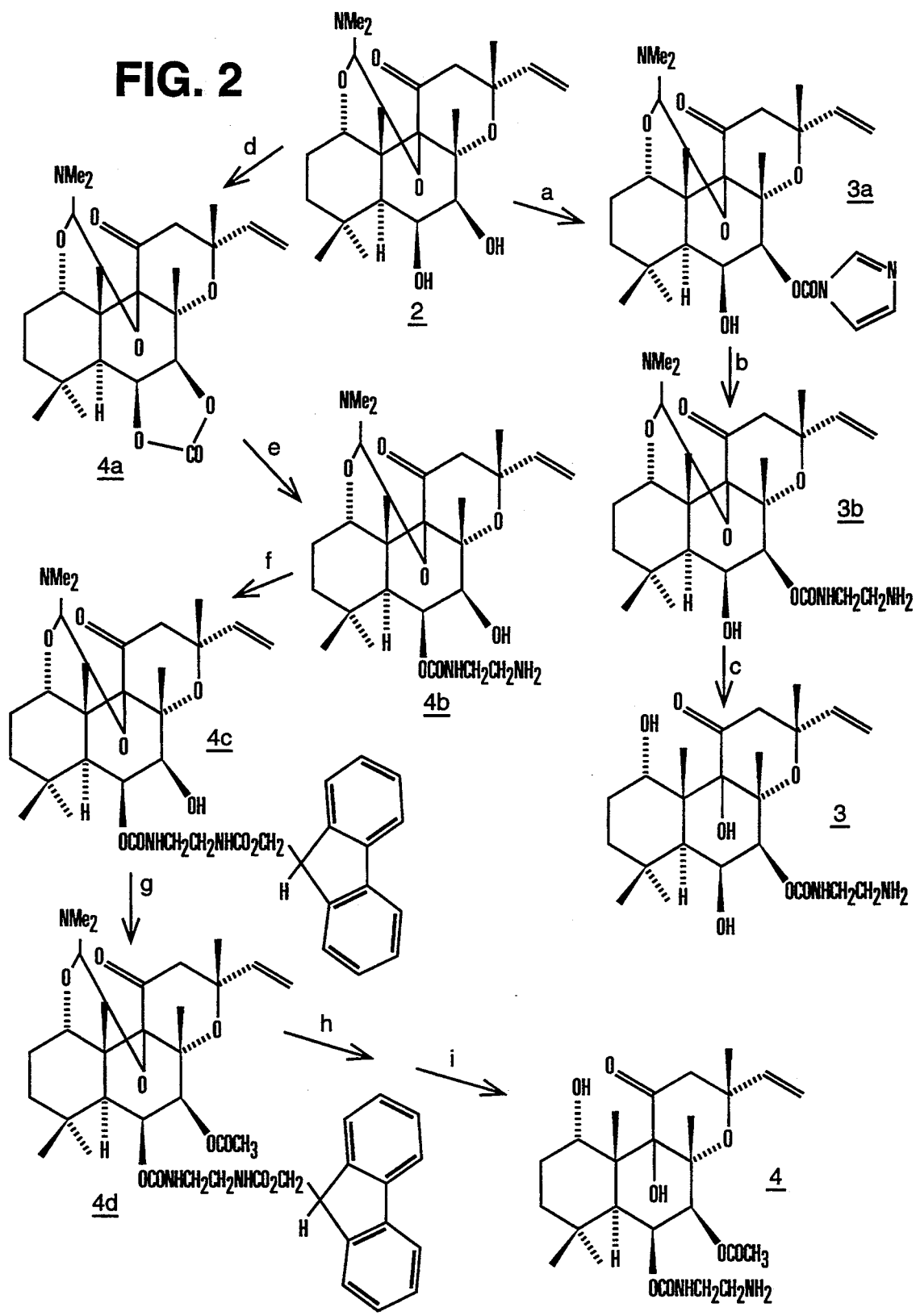
FIG. 2 shows the synthetic scheme used to synthesize 7-aminoethylcarbamylforskolin (compound 3), and 6-aminoethylcarbamylforskolin (compound 4) from the 1,9-dimethylformamide acetal of 7-desacetylforskolin (compound 2) which is the starting material.
Figure 3:
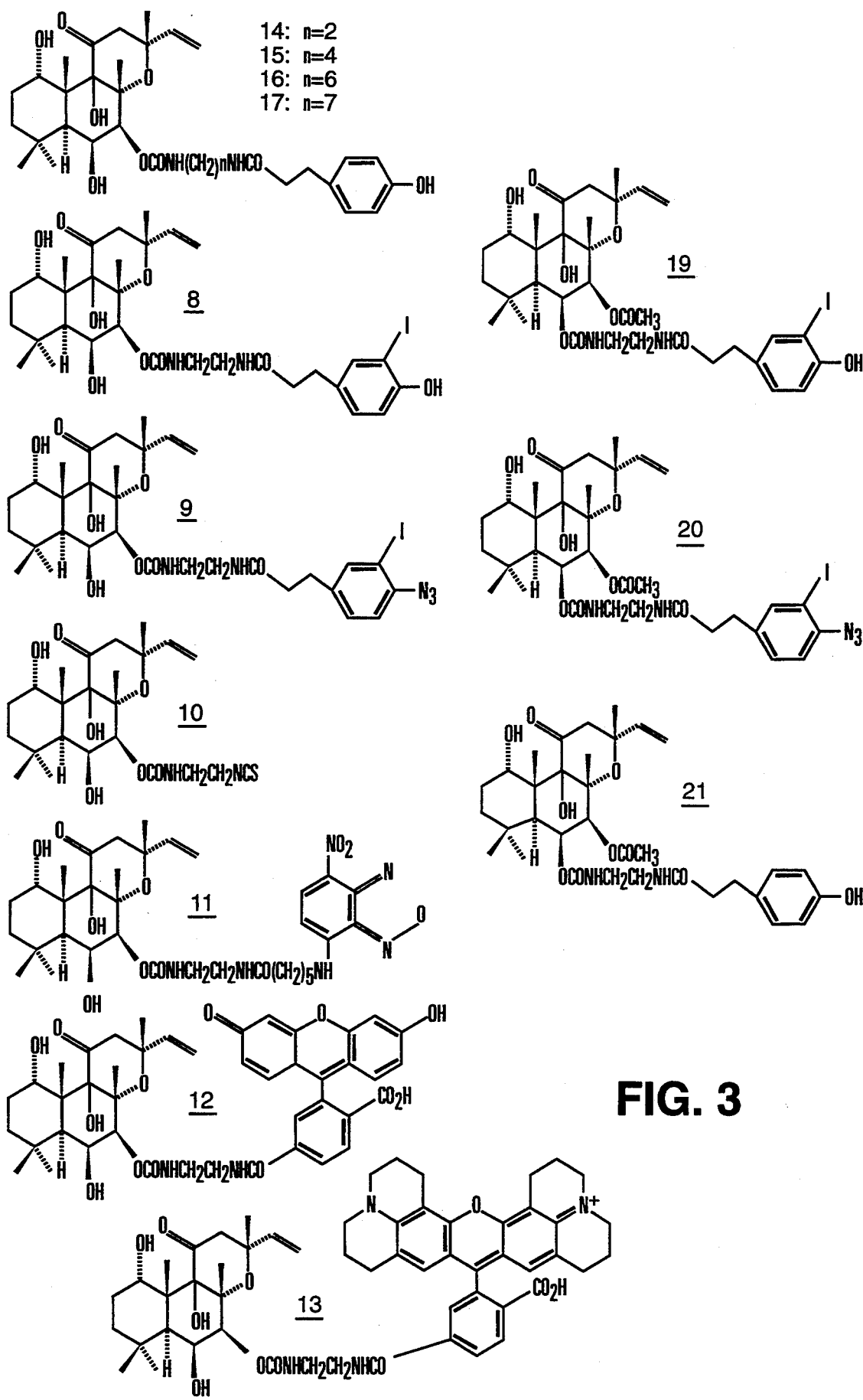
FIG. 3 shows the structures of derivatives of the aminoalkylcarbamates of forskolin.

The 7-aminoethylcarbamate can be synthesized using the 1,9-dimethylformamide acetal of 7-desacetylforskolin as starting material (see synthetic scheme of FIG. 2). The selective reactivity of carbonyldiimidazole (CDI) with the equatorial 7β-hydroxyl group is exploited to form the 7-acylimidazole intermediate. The reaction of the 7-acylimidazole intermediate with ethylenediamine produces the 7-aminoethylcarbamate of forskolin (see 3 in FIG. 1 and Example 1). The same procedure is carried out to produce 7β-aminobutylcarbamate (5), 7β-aminohexylcarbamate (6), and the 7β-aminoheptylcarbamate (7) of forskolin. The 7β-aminoalkylcarbamates of forskolin are very stable compounds. The 7β-aminoethylcarbamate of forskolin is stable to heating in 0.1N KOH in methanol for two hours at 60° C.

Derivatives of 7-desacetylforskolin that contain hydrophilic groups esterfied at the 6β-hydroxyl group are not potent at stimulating adenylate cyclase. In contrast, the same 6-acyl derivatives of forskolin (i.e., that contain an acetoxy group at the 7β-position) are very potent at adenylate cyclase. Therefore, the aminoethylcarbamate of 7-desacetylforskolin was synthesized and a procedure was developed to reacylate the 7β-hydroxyl group in order to form the 6-aminoethylcarbamate of forskolin (Example 2). The synthesis of the 6-aminoethylcarbamate of forskolin uses the 1,9-dimethylformamide acetal of 7-desacetylforskolin as starting material (see synthetic scheme of FIG. 2). Reaction of the 1,9-dimethylformamide acetal of 7-desacetylforskolin with CDI and triethylamine forms the cyclic 6,7-carbonate (4a). Nucleophilic ring opening of the 6,7-carbonate by primary or secondary amines has been shown to produce exclusively 6-carbamates. Therefore, reaction of the 6,7-carbonate with ethylenediamine produces the desired 6-aminoethylcarbamate product (4b). The free amine is blocked with fluorenylmethoxychloroformate (FMOC) prior to reacylation of the 7β-hydroxyl group with acetic anhydride. Removal of the formamide acetal blocking group with acetic acid in methanol followed by removal of the FMOC blocking group with piperidine produces the crystalline 6β-aminoethylcarbamate (4) of forskolin after purification on silica gel.

The 7-aminoethylcarbamate of 1,9-dideoxyforskolin can be synthesized using 1,9-dideoxyforskolin as the starting material. 1,9-Dideoxyforskolin is hydrolyzed in K$_2$CO$_3$ in methanol to produce 7-desacetyl-1,9-dideoxyforskolin. This compound is then reacted with CDI as described in Example 1 to form the acyl imidazolium intermediate. The 7-aminoethylcarbamate is formed after addition of ethylenediamine. The 7-aminoethylcarbamate of 1,9-didexoyforskolin (18) is purified using flash chromatography on silica gel.

The 1-aminoalkylcarbamate can be synthesized by reacting forskolin with carbonyldiimidazole to form the 1-acyl imidazole derivative. Reaction of the 1-aminoalkylcarbamate with a primary or secondary amine will produce the dersired 1-aminoalkylcarbamate of forskolin.

The 1-aminoalkylcarbamate has the formula:

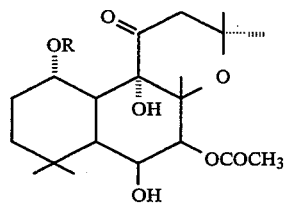

wherein R is CONH(R$_1$)NH$_2$ and R$_1$ is a hydrocarbon group of the formula (CH$_2$)$_n$ or CH$_2$CH=CH(CH$_2$)$_n$ wherein n=1, 2, 4, 5 or 7.

The 9-aminoalkylcarbamate of forskolin can be synthesized by reacting forskolin with carbonyldiimidazole in the presence of triethylamine to form the 1,9-cyclic carbonate of forskolin. The regioselective reaction of primary amines with the 1,9-cyclic carbonate of forskolin will produce the 9-aminoalkylcarbonate of forskolin.

The 9-aminoalkylcarbamate has the formula:

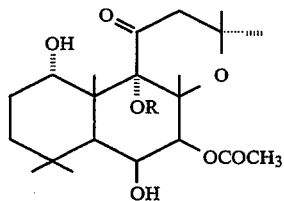

wherein R is CONH(R$_1$)NH$_2$ and R$_1$ is a hydrocarbon group of the formula (CH$_2$)$_n$ or CH$_2$CH=CH(CH$_2$)$_n$ wherein n=1, 2, 4, 5 or 7.

6,7-Carbamate derivatives of forskolin can be synthesized. 6-aminoalkylcarbamates of forskolin can be synthesized by reacting the 1,9-dimethylformamide acetal of 7-desacetylforskolin with carbonyldiimidazole to form the 6,7-carbonate. Regioselective ring opening of the 6,7-carbonate with ethylene diamine forms the 6-aminoethylcarbamate. The 6-aminoethylcarbamate is reacted with fluorenylmethoxychloroformate. This protected aminoalkylcarbamate (compound 4c in FIG. 2) is then reacted with carbonyldiimidazole to form the 7-acyl imidzolium intermediate. Reaction of the 7-acyl imidazolium derivative with a primary or secondary amine forms the mixed 6,7-carbamate of forskolin.

Using the above procedures, it is possible to synthesize 1-aminoalkylcarbamates, 9-aminoalkylcarbamates, 7-aminoalkylcarbamates, 6 aminoalkycarbamates, 6,7-diaminoalkylcarbamates, 1,6-diaminoalkylcarbamates, 1,7-diaminoalkylcarbamates, and 1,6,7-triaminoalkylcarbamates of forskolin.

The aminoalkylcarbamates of forskolin can be reacted with amine reactive groups such as N-hydroxysuccinimide activated esters to produce other derivatives of forskolin using standard reaction conditions (Example 3). The reactions are carried out rapidly (two hours at room temperature) and are quantitative. The products from the aminoalkylcarbamates and the activated esters can be completely separated from the starting materials by conventional flash chromatography on silica gel.

More specifically, the derivatives can be produced by dissolving the aminoalkylcarbamate intermediate in a minimum volume of organic solvent having a concentration of approximately 5 mg/mL. An activated ester, such as N-hydroxysuccinimide ester, is added to the solution at a 1.5 molor ratio to the aminoalkylcarbamate. The reaction is allowed to proceed at room temperature for 2 hours. The derivative is then purified by silica gel chromatography.

A derivative produced in such a manner has the formula:

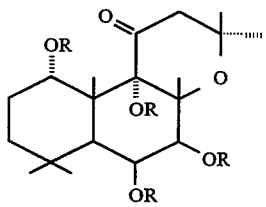

wherein R=CONH($R_1$)$NH_1$($R_2$) or H and $R_1$ is an alkyl group of formula $(CH_2)_n$ or $CH_2CH=CH(CH_2)_n$, n=1, 2, 4, 5 or 7, $R_2$ is a ligand or functional group of the formula

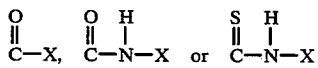

and X is a fluorescent group or any other functional group.

7-Aminoethylcarbamylforskolin can be reacted with commercially available Bolton Hunter reagent (the N-hydroxysuccinimide ester of (3-(3-$^{125}$I-4 hydroxyphenyl)propionic acid, 2200 Ci/mmol) using the standard reaction conditions (Example 3) to form derivative 8 (7-$^{125}$I-HPP-Fsk). This derivative of forskolin is easily separated from the starting materials and is synthesized carrier free with a specific activity of 2200 Ci/mmol.

7β-Aminoethylcarbamylforskolin can be reacted with (3-(3-$^{125}$I-4-aziaophenyl)propionic acid, 2200 Ci/mmol) using the standard reaction conditions (Example 3) to form derivative 9 (7-AIPPS-Fsk). This derivative is a photoactivatable derivative of forskolin with radioactive iodine with a specific activity of 2200 Ci/mmol.

7β-Aminoethylcarbamylforskolin, 7β-aminobutylcarbamylforskolin, 7β-aminohexylcarbamylforskolin, and 7β-aminoheptylcarbamylforskolin are reacted with the N-hydroxysuccinimide activated ester of 3-(4-hydroxyphenyl)propionic acid to produce derivatives 14, 15, 16, 17 using the standard reaction conditions (Example 3).

Fluorescent derivatives of 7-aminoethylcarbamylforskolin can be synthesized by reaction with the N-hydroxysuccinimide activated esters of fluoresceine, rhodamine, and NBD to produce derivatives 11, 12, 13.

6-Aminoethylcarbamylforskolin can be reacted with commercially available Bolton Hunter reagent (N-hydroxysuccinimide ester of (3-(3-$^{125}$I-4-hydroxyphenyl)propionic acid, 2200 Ci/mmol) using the standard reaction conditions (Example 3) to form derivative 19 (6-$^{125}$I-HPP-Fsk). This derivative of forskolin is easily separated from the starting materials and is synthesized carrier free with a specific activity of 2200 Ci/mmol.

6-Aminoethylcarbamylforskolin can be reacted with (3-(3-$^{125}$I-4-azidophenyl)propionic acid, 2200 Ci/mmol) using the standard reaction conditions (Example 3) to form derivative 20 (6-AIPPS-Fsk). This derivative is a photoactive derivative of forskolin with radioactive iodine and has a specific activity of 2200 Ci/mmol.

6-Aminoethylcarbamylforskolin can be reacted with the N-hydroxysuccinimide ester of 3-(4-hydroxyphenyl)propionic acid using the standard reaction conditions to form derivative 21.

The aminoalkylcarbamates can also be coupled to solid supports. 7-Aminoethylcarbamylforskolin can be coupled to the commercially available cross linked agarose resin Affigel 15 to form the solid support shown as derivative 22 (example 4). The reaction is quantitative and all of the 7-aminoethylcarbamylforskolin is coupled to the resin.

6-Aminoethylcarbamylforskolin can be coupled to the commercially available cross linked agarose resin Affigel 15 to form the solid support shown as derivative 23 (example 4). This reaction is also quantitative, and all of the 6-aminoethylcarbamylforskolin is coupled to the resin.

There is currently only one direct binding assay for measuring the amount of adenylate cyclase (Seamon et al., *Proc. Natl. Acad. Sci.*, 81:5081 (1984)). This assay uses 12-[$^3$H]-forskolin which has a specific activity of about 30 Ci/mmol. The low specific activity of the ligand precludes the use of this assay for measuring adenylate cyclase when there are only low amounts of tissue available. It would be extremely desirable to have a ligand that would bind to adenylate cyclase with a high affinity which would also have a high specific activity.

Figure 4:
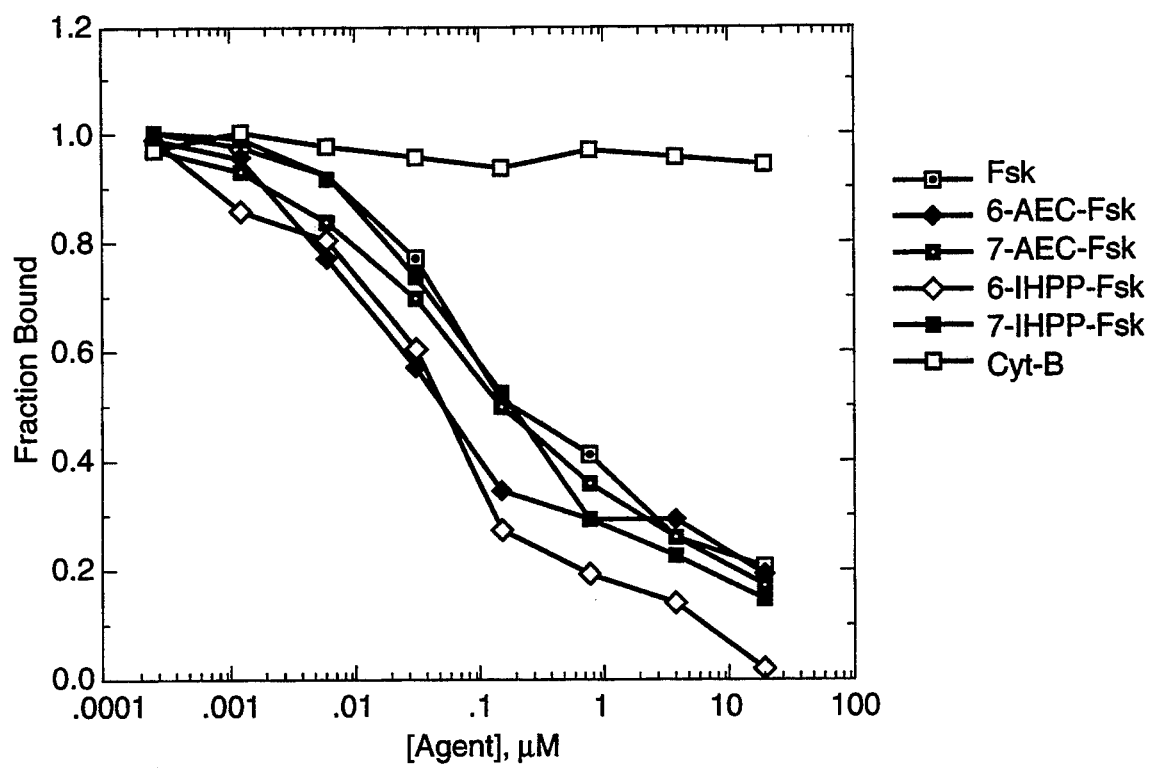
FIG. 4 shows the inhibition of binding of $^{125}$I-labelled derivative 19 to bovine brain membranes by forskolin (Fsk), 6-aminoethyl forskolin (6-AEC-Fsk), 7-aminoethylforskolin (7-AEC-Fsk), compound 19, compound 8, and cytochalasin B.

Derivative 19 (6-$^{125}$I-HPP-Fsk) was used to develop a binding assay for adenylate cyclase (Example 4). 6-$^{125}$I-HPP-Fsk binds to membranes from bovine brain and human platelets with a Kd of about 25 nM (FIG. 4). Therefore, a filtration assay can be used to separate the bound from free ligand and determine the amount of high affinity binding. The binding of 6-$^{125}$I-HPP-Fsk to membranes is inhibited by forskolin, but not by 1,9-dideoxyforskolin which is consistent with these binding sites being associated with adenylate cyclase. The binding of 6-$^{125}$I-HPP-Fsk is not inhibited by D-glucose or cytochalasin B which indicates that 6-$^{125}$I-HPP-Fsk is not binding with high affinity to the glucose transporter in brain tissue. Analogs of forskolin that activate adenylate cyclase inhibit the binding of 6-$^{125}$I-HPP-Fsk to membranes. The ability of an agent to inhibit 6-$^{125}$I-HPP-Fsk binding to membranes is therefore indicative of its ability to stimulate adenylate cyclase.

The binding of 6-$^{125}$I-HPP-Fsk is specific for adenylate cyclase. The amount of 6-$^{125}$I-HPP-Fsk bound to a tissue is therefore representative of how much adenylate cyclase is present in the tissue. It is possible to use the technique described in example 4 for determining the amount of adenylate cyclase in tissues.

Furthermore, there is currently only one assay for the direct measurement of the glucose transporter (Cushman et al., *J. Biol. Chem.* 255:4758 (1980)). This assay measures the amount of tritiated cytochalasin B that is bound to membranes and is displaced by D-glucose. The assay has a number of experimental problems which make it unsuitable for routine use. The radioactive cytochalasin B is tritiated and has a low specific activity. Therefore, a lot of protein is required for the assay. The affinity of cytochalasin B for the glucose transporter is about 1 μM and therefore the free label must be separated from the bound label using a centrifugation assay which is time consuming and leads to problems in defining non-specific binding.

Figure 5:
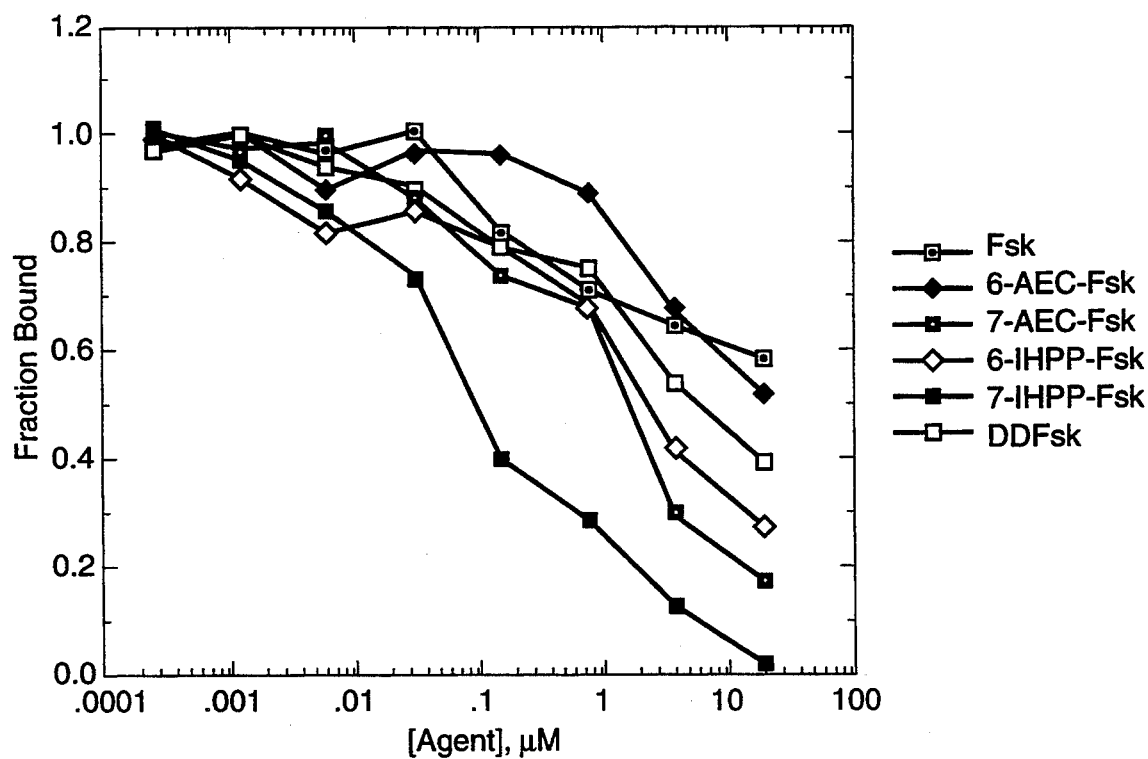
FIG. 5 shows the inhibition of binding $^{125}$I-labelled derivative 8 to membranes from human red blood cells by forskolin (Fsk), 6-aminoethylforskolin (6-AEC-Fsk), 7-aminoethylforskolin (7-AEC-Fsk), compound 19, compound 8 and 1,9-dideoxyforskolin.
Figure 6:
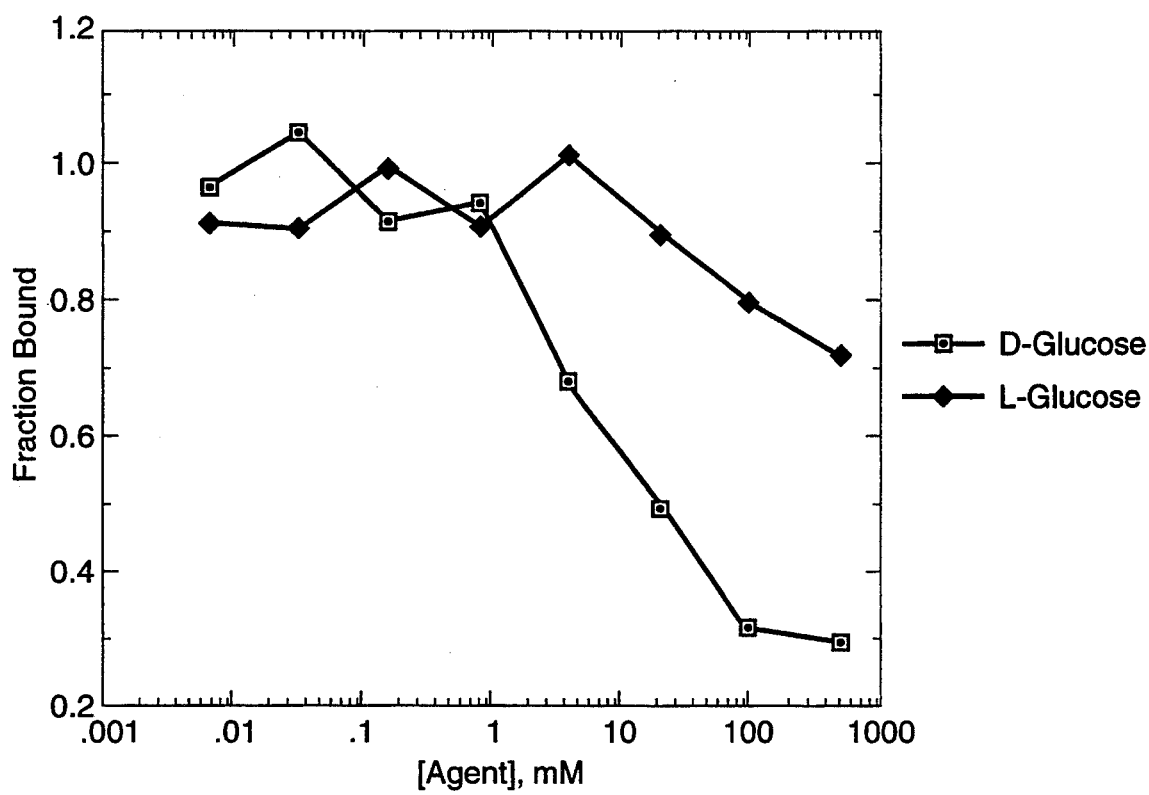
FIG. 6 shows the inhibition of binding of $^{125}$I-labelled derivative 8 to membranes from human red blood cells by D-glucose but not by L-glucose.
Figure 7:
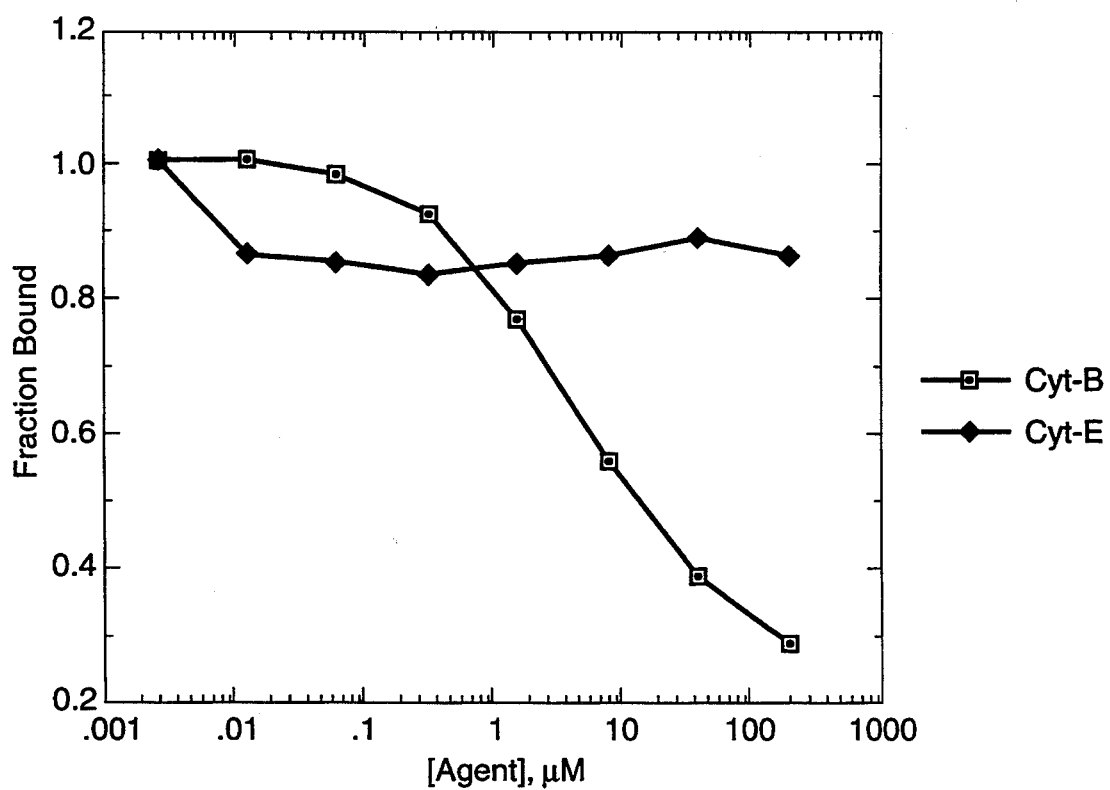
FIG. 7 shows the inhibition of binding of $^{125}$I-labelled derivative 8 to membranes from human red blood cells by cytochalasin B but not by cytochalasin E.

It would be extremely desirable to have a ligand that would bind to the glucose transporter with a high affinity which would also have a high specific activity. Derivative 8 (7-$^{125}$I-HPP-Fsk) binds to membranes from human red blood cells with an affinity of 30 nM (Example 5). The bound 7-$^{125}$I-HPP-Fsk can be separated from the free 7-$^{125}$I-HPP-Fsk using a filtration assay which is rapid and reproducible. The binding of 7-$^{125}$I-HPP-Fsk to membranes from human red blood cells is inhibited by forskolin and other analogs of forskolin that bind to the glucose transporter (FIG. 5). The binding of 7-$^{125}$I-HPP-Fsk is inhibited by D-glucose but not L-glucose and by cytochalasin B but not by cytochalasin E (FIGS. 6 and 7). The glucose transporter binds D-glucose and cytochalasin B but not L-glucose or cytochalasin E. Therefore, 7-$^{125}$I-HPP-Fsk binds to the human red blood cell glucose transporter with high affinity.

7-$^{125}$I-HPP-Fsk also binds with high affinity to other tissues including bovine brain, rat heart, rat muscle, and human platelets. The binding of 7-$^{125}$I-HPP-Fsk to these tissues is inhibited by D-glucose and cytochalasin B. Therefore, 7-$^{125}$I-HPP-Fsk binds with high affinity to the glucose transporter in diverse tissues. The high affinity binding of 7-$^{125}$I-HPP-Fsk to tissues as described in Example 5 will be indicative of the amount of glucose transporter and will not detect adenylate cyclase.

Photoactivatable derivatives of forskolin can also be synthesized.

Derivative 9 (7-AIPPS-Fsk) is incubated with human red blood cell membranes, photolyzed, and then the radioactive proteins were analyzed by SDS gel electrophoresis. The 7-AIPPS-Fsk labels the glucose transporter in these membranes and the labelling is inhibited by D-glucose and cytochalasin B. The 7-AIPPS-Fsk is more potent at labelling the glucose transporter in human red blood cell membranes than 6-AIPPS-Fsk.

Derivative 20 (6-AIPPS-Fsk) is incubated with partially purified preparations of bovine brain adenylate cyclase, photolyzed, and then the radioactive proteins are analyzed by SDS gel electrophoresis. The 6-AIPPS-Fsk is covalently incorporated into the adenylate cyclase. This labelling is inhibited by forskolin but not by 1,9-dideoxyforskolin, cytochalasin B, or D-glucose. 6-AIPPS-Fsk can also label adenylate cyclase in crude membranes. 6-AIPPS-Fsk is incubated with bovine brain membranes, photolyzed, and the radioactive proteins are analyzed by SDS gel electrophoresis. The 6-AIPPS-Fsk labels the adenylate cyclase in bovine brain membranes and this labelling is not inhibited by 1,9-dideoxyforskolin. The 7-AIPPS-Fsk is less efficient at labelling the adenylate cyclase than the 6-AIPPS-Fsk.

Membranes from a human ovarian carcinoma cell line that overexpress the P-glycoprotein can be incubated with derivative 20 (6-AIPPS-Fsk), photolyzed, and the radioactive proteins analyzed by SDS gel electrophoresis. The P-glycoprotein which is overexpressed in these cells and is associated with multi drug resistance in cancer cell lines, is labelled by 6-AIPPS-Fsk. The labelling is inhibited by adriamycin and other drugs that bind to the P-glycoprotein. The lipophilic derivative 21 (6-HPP-Fsk) and 1,9-dideoxyforskolin are more potent at inhibiting the labelling by 6-AIPPS-Fsk than forskolin. These results indicate that the forskolin binding site on the P-glycoprotein has an enhanced affinity for lipophilic derivatives of forskolin.

In view of the above discussion, it is apparent that aminoalkylcarbamates of forskolin can be synthesized and are quite stable. Two intermediates have been synthesized and used to produce derivatives of forskolin. Derivatives of the intermediate 6-aminoethylcarbamylforskolin have high affinity and selectivity for adenylate cyclase and lower affinity for the glucose transporter. In contrast, derivatives of the intermediate 7-aminoethylcarbamylforskolin have high affinity for the glucose transporter and have low affinity for adenylate cyclase. Thus these two derivatives demonstrate that aminoalkylcarbamates of forskolin are stable and reactive intermediates for producing derivatives of forskolin with selectivity at different forskolin sites of action.

The unique properties of the aminoalkylcarbamates can be used to produce derivatives of forskolin for the following purposes.

Forskolin derivatives have been investigated for the treatment of bronchodilation, glaucoma, and heart diseases. However, forskolin binds to the glucose transporter in human red blood cells. Derivatives of 6-aminoethylcarbamylforskolin would bind very tightly to adenylate cyclase and have a lower affinity for the glucose transporter in human red blood cells. Therefore, derivatives of 6-aminoethylcarbamylforskolin could be administered to produce therapeutic effects without effects due to actions at the glucose transporter.

Figure 8:
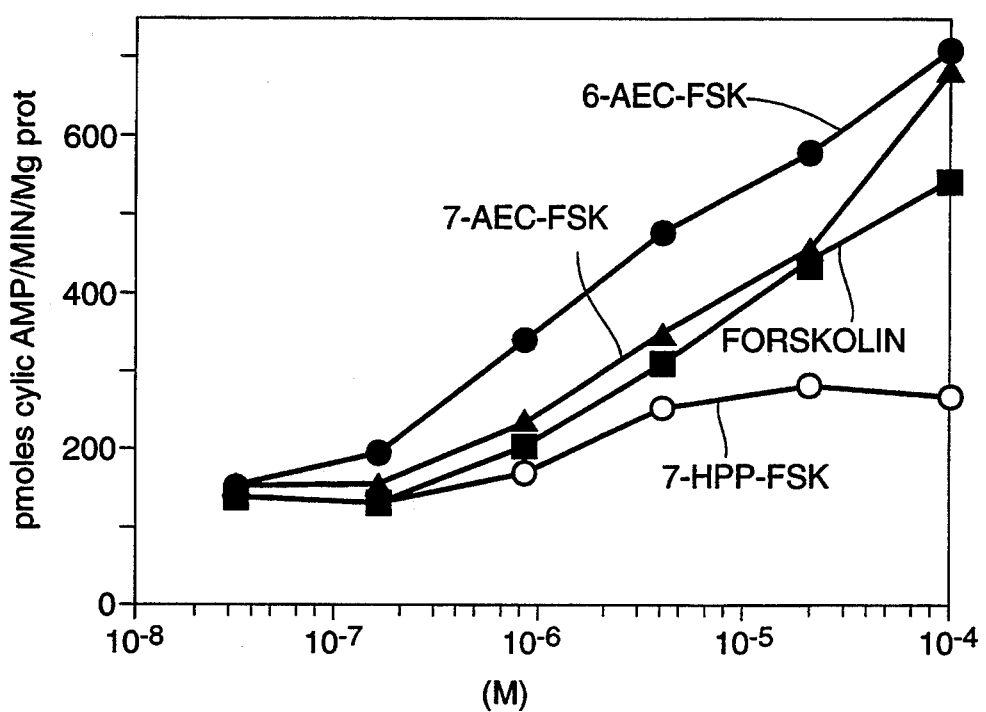
FIG. 8 shows the activation of bovine brain adenylate cyclase by forskolin, 7-aminoethylcarbamylforskolin, 6-aminoethylcarbamylforskolin, and derivative

The aminoalkylcarbamates of forskolin stimulate adenylate cyclase with the same EC50 as forskolin (FIG. 8). However, 7-aminoethylcarbamylforskolin and 6-aminoethylcarbamylforskolin stimulate adenylate cyclase to a greater extent than forskolin because of their enhanced water solubility. Therefore, these compounds would be more useful as therapeutic agents than forskolin, since they are more water soluble and could produce a more rapid effect in vivo. Thus, these compounds or their salts would be very useful positive inotropic agents.

Forskolin and derivatives of 6-aminoethylcarbamylforskolin bind to the P-glycoprotein. This protein is responsible for the energy dependent export of drugs from cancer cells and may be responsible for the resistance of certain types of tumors to chemotherapy. Forskolin and 1,9-dideoxyforskolin can sensitize certain cancer cells to the cytotoxic effects of drugs (Wadler et al., *Cancer Res.* 48:539 (1988)). Lipophilic derivatives of forskolin and 1,9-dideoxylforskolin are potent at inhibiting the labelling of the P-glycoprotein by derivative 20. 6-Aminoethylcarbamyl-1,9-dideoxylforskolin could be synthesized as described in Example 2. This intermediate could then be reacted with 3-(4-hydroxyphenyl)propionic acid to form a lipophilic derivative of 1,9-dideoxylforskolin. This derivative would be potent at the P-glycoprotein activation of adenylate cyclase. This derivative could then be administered with chemotherapeutic agents and produce a sensitization to the chemotherapeutic drug.

Forskolin and derivatives of aminoalkylcarbamates of forskolin can interact with a diverse group of membrane transport proteins. It is likely that most transport proteins will be affected by forskolin and forskolin derivatives. Lipophilic derivatives of aminoalkylcarbamates of 1,9-dideoxyforskolin could be produced and used to block membrane transport proteins which would result in therapeutic effects without side effects due to adenylate cyclase activation. These could be used to block the monoamine uptake system and therefore be useful drugs for the treatment of schizophrenia of depression. These derivatives would have the potential to block ion loss through interactions with the Clchannel transporter associated with the defect in cystic fibrosis.

Derivatives of 7-aminoalkylcarbamates of forskolin (or 1,9-dideoxyforskolin) are potent at the glucose transporter and are not potent at adenylate cyclase. Derivatives of 7-aminoalkylcarbamates would be useful for blocking glucose uptake without the side effects due to the stimulation of adenylate cyclase.

Derivatives of 7-aminoalkylcarbamates of forskolin can be used to measure the levels of the glucose transporter in tissues in monitoring the response of therapeutic strategies such as insulin, diet, exercise, and other drugs that are used in treating diabetes. For example, tissue could be removed and membranes made from the tissue. The radioactive 7-$^{125}$I-HPP-Fsk bound to the tissue could be quantitated by determining the amount of radioactive material bound to the membrane as demonstrated in Example 6.

Tumors are sometimes resistant to different classes of drugs. It is thought that this multi-drug resistance is due to the presence of a membrane protein called the P-glycoprotein. Derivatives of 6-aminoalkylcarbamates could be used to measure the amount of the P-glycoprotein in biopsies. Tumor samples could be removed, radioactive 19 (6-$^{125}$I-HPP-Fsk) could be added to the samples and the amount of 6-$^{125}$I-HPP-Fsk bound to the membranes (determined as described in Example 5) would be diagnostic of the amount of P-glycoprotein expressed in the specific tumor. Drugs that are able to displace 6-$^{125}$I-HPP-Fsk from the tumor membranes would be expected to be transported from the tumors by the P-glycoprotein. Therefore, these drugs might be sensitized by the presence of forskolin or forskolin derivatives.

Furthermore, a forskolin derivative can also be utilized to measure the P-glycoprotein in a tissue sample by, first, synthesizing a radioactive derivative of 6-aminoalkylcarbamyl-1,9-dideoxyforskolin, 1,9-dideoxy forskolin. Membranes must then be extracted from biopsy samples taken from tumors. The radioactive derivative of 6-aminoalkylcarbamyl-1,9-dideoxyforskolin must then be added to the membranes. Finally, the amount of radioactive derivative that is bound to the tissue sample is measured using a filtration assay to separate the bound from the free ligand.

Derivatives of aminoalkylcarbamates of forskolin can be used for the histopathological analysis of tissue samples. Fluorescent derivatives of 7-aminoalkylcarbamates have been synthesized (11, 12, 13) and can be added to slide mounted tissue sections. The fluorescent staining would be indicative of the location of the glucose transporter. A similar technique could be used to localize other forskolin binding proteins. Fluorescent derivatives of 6-aminoalkylcarbamates could be used to stain adenylate cyclase. Fluorescent derivatives of 6-aminoalkylcarbamates of 1,9-dideoxforskolin could be used to stain tissues for localizing the P-glycoprotein in tumor samples.

Fluorescent derivatives of forskolin can also be used to visualize forskolin binding proteins in tissue samples.

A fluorescent derivative of forskolin can be synthesized by reacting an aminoalkylcarbamate of forskolin with an activated ester (or an isothiocyanate) of a fluorescent molecule. The fluorescent derivative is added to tissue samples that are mounted on slides, and the slides are then examined under fluorescence microscopy to visualize the forskolin binding protein.

Fluorescent derivatives of forskolin such as 11, 12 or 13 can be added to cell suspensions. The cells could then be analyzed using computerized laser cell sorters. The amount of forskolin binding proteins in the cell population could be determined in this matter. For example, the amount of glucose transporter present in platelets could be determined by adding 11 to a cell suspension and analyzing the cells by cell sorting.

More specifically, a fluorescent derivative of forskolin can be synthesized by first reacting an aminoalkylcarbamate of forskolin with an activated ester (or an isothiocyanate) of a fluorescent molecule. The fluorescent derivative of forskolin is then added to cells, and the cells are then analyzed by cell sorting to determine the amount of cells that bind the fluorescent derivative.

Aminoalkylcarbamates of forskolin or 1,9-dideoxyforskolin can be reacted with N-hydroxysuccinimide esters of biotin which are commercially available as described in Example 3. The biotin labelled forskolin derivatives could be added to tissue sections and the localization of the forskolin binding protein determined by adding avidin (which binds biotin with high affinity) that is coupled to an appropriate detection system.

Iodinated derivatives of forskolin can be used for in vivo imaging of forskolin binding proteins. For example, 21 can be iodinated with Na$^{123}$I using chloramine T catalyzed oxidation to produce the $^{123}$I-labelled 19. This compound could be administered at very low doses in humans, and the localization of the compound would be indicative of the levels of adenylate cyclase. The localization of the compound could be determined by in vivo spec scanning. It is possible to produce $^{123}$I-labelled 14–17 using the chloramine T oxidation and commercially available Na$^{123}$I. These iodinated compounds could be used for the in vivo determination of the glucose transporter. Heart and muscle have extremely high concentrations of the glucose transporter. The iodinated derivatives could be given in extremely low doses and used to measure the ability of the heart and muscle to take up glucose. These derivatives might make very good spec scanning imaging agents.

Derivatives of aminoalkylcarbamates can also be used to screen for therapeutic agents.

A method of screening for drugs that can bind to forskolin binding proteins includes, first, reacting a derivative of an aminoalkylcarbamate of forskolin with a reactive derivative of biotin, in order to produce a biotin conjugated derivative. The biotin conjugated forskolin derivative is then added to a test sample. The biotin conjugated forskolin derivative that is bound to the test sample is separated from the free biotin conjugated forskolin derivative. The bound biotin conjugated forskolin derivative is then quantitated by adding avidin which has been conjugated with a suitable detection system (which is commercially available).

Derivatives of 6-aminoalkylcarbamates bind with high affinity to adenylate cyclase. A binding assay can be developed using derivatives of 6-aminoalkylcarbamates as described in Example 4. The ability of a drug to inhibit the binding of 6-aminoalkylcarbamates to membranes will reflect its ability to activate adenylate cyclase.

Iodinated or fluorescent labelled derivatives of 6-aminoalkylcarbamates of 1,9-dideoxylforskolin can be synthesized as described in Example 2 and 3. These derivatives will have high affinity for the P-glycoprotein. The ability of drugs to inhibit the binding of such derivatives will reflect their potency at the P- glycoprotein and their ability to act as sensitizers for chemotherapeutics. Membranes from cell lines that overexpress the P-glycoprotein can be prepared. The derivative of forskolin or 1,9-dideoxyforskolin can be added to the membranes in the presence of a test drug. The amount of derivative bound to the membrane can be determined by a filtration assay (or other assay). The amount of derivative bound to the membrane will be decreased if the test drug binds to the P-glycoprotein.

Derivatives of 7-aminoalkylcarbamates of forskolin bind with high affinity to the glucose transporter (Example 5). The ability of drugs to inhibit the binding of such derivatives of human and red cell membranes will be indicative of their ability to inhibit glucose transport and uptake.

Alkylating derivatives of the aminoalkylcarbamates can be synthesized to produce derivatives that will react covalently with forskolin binding proteins. Reaction of aminoalkylcarbamates with thiophosgene will produce the isothiocyanates that are reactive to nucleophillic groups on proteins. The isothiocyanates can react covalently with the protein to block the binding site. This can be used to block the binding or transport of drugs. For example, the isothiocyanate of 6-aminoethylcarbamyl-1,9-dideoxyforskolin could be administered to patients and would bind to the P-glycoprotein. This would then bind irreversibly to the P-glycoprotein binding site and block the efflux of cancer drugs from the tumor cell.

Alkylating derivatives of adenylate cyclase can be produced by the reaction of 6-aminoalkylcarbamates with thiophosgene. These alkylating agents can be used to inhibit hormonal stimulation of adenylate cyclase in tissues that are hyper-responsive to hormones.

Alkylating derivatives of 7-aminoalkylcarbamates can be produced by the reaction of 7-aminoalkylcarbamates with thiophosgene. These derivatives can be used to irreversibly block glucose uptake in cells that overexpress forms of the glucose transporter that can be alkylated.

Additionally, aminoalkycarbamates of forskolin can be coupled to carrier proteins in order to increase their specificity for particular cells. For example, 7-aminoethylcarbamylforskolin could be reacted with thiophosgene to form the isothiocyanate derivative, 10. This derivative could then be added to a monoclonal antibody directed against a specific cell surface marker. The derivative 10 would react with amino groups on the monoclonal antibody, forming a stable conjugate with the protein. This conjugate could then be used to deliver forskolin to specific cell types.

Aminoalkylcarbamates can be reacted with succinic anhydride to form the hemi-succinate derivatives. These hemi-succinate derivatives could be coupled to proteins using carbodimide coupling which would produce conjugates of forskolin covalently attached to proteins through stable amide bonds.

Based on the above discussion, it is apparent that the aminoalkylcarbamate intermediates of the present invention can be used to produce forskolin derivatives which can, in turn, be utilized as ligands. Such ligands have specificity for different forskolin binding proteins, and can only be created using the aminoalkylcarbamate intermediates.

EXAMPLE 1

Synthesis of 7-Aminoethylcarbamylforskolin (3) from Dimethylformamideacetal-7-desacetylforskolin (7-AEC-Fsk)

1,9-Dimethylformamideacetal-7-desacetylforskolin

The compound is readily synthesized from forskolin. 400 mg of forskolin is dissolved in 3 mL dimethylformamide dimethyl acetal and reacted under argon for 4 hours at room temperature and overnight at 55° C. The product is extracted into methylene chloride and dried to an oil. The crude compound is dissolved in chloroformethyl acetate (8:2) and purified on silica gel in that solvent system. The 7-acetyl group is removed by hydrolyzing overnight at room temperature in 0.06% $K_2CO_3$ in 60% methanol. The purified 2 is recovered by extraction into methylene chloride and drying under vacuum.

7-Aminoethylcarbamate-7-desacetyl-forskolin(3)

57.4 mg of carbonylimidazole is added to 100 mg of 2 dissolved in 2 mL of methylene chloride. The reaction is stirred at room temperature for 4–6 hours yielding 3a. Ethylenediamine (78.7 μL) is added and the reaction is allowed to stir overnight producing 2b. The reaction is diluted in methylene chloride and washed with water. The organic layer is removed and taken to dryness under vacuum. The dimethylformamide acetal is removed by dissolving the residue in 2 ml 80% acetic acid (v/v in methanol) and hydrolyzing overnight yielding the crude final product 3. The reaction is neutralized with $K_2CO_3$, extracted with methylene chloride and dried. The residue is dissolved in a minimum of chloroform and 2 is purified on silica gel developed with chloroform/methanol/triethylamine (9:1:0.1). $^1$H-NMR(CDCl$_3$/TMS) for 3: δ5.92–6.01(dd, 1H, H-14), 5.33 (d, 1H,H-15), 5.24 (d, 1H, H-7), 5.00 (d, 1H, H-15), 4.5–4.9 (m, 2H, H-1, H-6), 3.27 (m, 2H, —NHCH$_2$CH$_2$NH$_2$), 3.20(d, 1H, H-12), 2.86(t, 2H, —NHCH$_2$CH$_2$NH$_2$), 2.48 (d, 1H, H-12), 2.18(d, 1H, H-5), 1.75 (s, 3H, CH$_3$), 1.43 (s, 3H, CH$_3$), 1.37 (s, 3H, CH$_3$), 1.26 (s, 3H, CH$_3$), 1.05 (s, 3H, CH$_3$).

EXAMPLE 2

Synthesis of 6-aminoethylcarbamylforskolin (4) from dimethylformamide-7-desactetylforskolin (See FIG. 2)

6-Aminoethylcarbamate-7-desacetyl-1,9-dimethylformamide-acetal-forskolin (4b)

Triethylamine (92.7 μL) and carbonylimidadole (57.4 mg) are added to 100 mg of 2 dissolved in 2 mL of methylene chloride. The reaction is stirred overnight and is monitored by TLC on silica gel. The reaction is allowed to proceed until the 6,7-carbonate derivative, 4a has formed. Ethylenediamine (78.7 μL) is added and the reaction is stirred at room temperature overnight yielding 4b. The reaction is washed with water and the organic layer is dried under vacuum.

6-FMOC-aminoethylcarbamyl-7-desacetyl-1,9-dimethylformamideacetalforskolin (4c)

4b is dissolved in 2 mL of methylene chloride, 39 μL of triethylamine and 79 mg of fluorenylmethoxychlorofomate (FMOC) are added. The reaction is stirred on ice for 2 hours, dried and the product 4c is purified by chromatography on silica gel with hexane/ethyl acetate (4:6).

6-aminoethylcarbamylforskolin (4)

A crystal of DMAP and 100 μL of acetic anhydride are added To 4c, dissolved in 1 mL methylene chloride and 110 μL of pyridine. The reaction is stirred at room temperature overnight, yielding 4d. The solvent is removed under vacuum. The residue is brought up in methylene chloride, washed with 0.001M sodium bicarbonate, and dried. The acetal blocking group is removed by hydrolysis overnight in 2 mL of 80% acetic acid (v/v in methanol). The reaction is washed with water and dried. The residue is dissolved in 2 mL methylene chloride and 200 μL of piperidine is added to remove the FMOC group. The reaction is stirred at room temperature for 45 minutes and dried. 4 is purified on silica gel developed with chloroform/methanol (9:1).

$^1$H-NMR (CDCl$_3$/TMS) for 4: δ5.9–5.99(dd, 1H, H-14), 5.68 (t, 1H, H-6), 5.49 (d, 1H, H-7), 5.30(d, 1H, H-15), 5.00 (d, 1H, H-15), 4.60(t, 1H, H-1), 3.27 (t, 2H, —NHCH$_2$CH$_2$NH$_2$), 3.23 (d, 1H, H-12), 2.84 (t, 2H, —NHCH$_2$CH$_2$NH$_2$), 2.45 (d, 1H, H-12), 2.36 (d, 1H, H-5), 2.04 (s, 3H, OCOCH$_3$), 1.65 (s, 3H, CH$_3$), 1.40 (s, 3H, CH$_3$), 1.35 (s, 3H, CH$_3$), 1.06 (s, 3H, CH$_3$), 1.00 (s, 3H, CH$_3$).

EXAMPLE 3

Standard Reaction Conditions for Reacting Aminoalkylcarbamates of Forskolin with N-Hydroxysuccinimide Activated Esters The aminoalkylcarbamate of forskolin (for example, intermediate 3 or 4) is dissolved in methylene chloride (or dimethylformamide). A 1.5 molar equivalent of the activated ester (for example, N-hydroxysuccinimidyl-3-(3-hydroxyphenyl)propionate) is added to the reaction and is allowed to stir at room temperature. The derivative of forskolin is purified by flash chromatography on silica gel with ethylacetate as solvent. This procedure has been used to prepare a number of derivatives of forskolin (see FIG. 3).

EXAMPLE 4

Attachment of Aminoalkylcarbamates to Solid Supports

This procedure reacts Affigel 15 (crosslinked agarose with activated esters attached to the resin) with aminoalkylcarbamates of forskolin. The reaction is carried out with 2 μmole of aminoalkylcarbamate per mL of resin. Reactive groups remaining after reaction with the aminoalkylcarbamates are reacted with 0.1M ethanolamine.

25 mL of Affigel 15 (approximately 15 μmole of reactive ester/mL) is washed on a coarse, sintered glass funnel with 150 mL of dry DMF. The resin is washed under vacuum but the vacuum is controlled so as not to dry out the resin. The moist resin is transferred to a polypropylene container (either 50 mL culture tube or freezer box) and is resuspended with an equal volume of dry DMF (25 mL). 50 μmole of the aminoethylcarbamyl derivative of forskolin is dissolved in 5 mL of dry DMF. The aminoalkylcarbamate of forskolin is added to the resin suspension over a five minute period of 0.5 mL aliquots mixing the suspension after each addition. The reaction is allowed to proceed for four hours at room temperature. Ethanolamine (0.3 mL) is added to the reaction and allowed to incubate 30 minutes. The suspension is transferred to a coarse, sintered glass funnel and washed with 300 mL of dry DMF, 300 mL of distilled water, and then stored refrigerated in distilled water.

EXAMPLE 5

Filtration Binding Assay for Adenylate Cyclase using Derivative 19 (6-$^{125}$I-HPP-Fsk)

Binding of 6-$^{125}$I-HPP-Fsk to Membranes—Crude membranes from bovine brain were incubated for 60 minutes at 60 minutes at 20° C. with 20,000 cpm of 6-$^{125}$I-HPP-Fsk. Binding equilibrium was reached by 45 minutes and was constant for at least 2 hours (data not shown). The incubations were carried out at 20° C. for 60 minutes in 12×75 glass test tubes in a total volume of 0.4 mL 50 mL Tris-HCl buffer, pH 7.4. The membranes (0.40 mg/tube) were incubated in the presence of 5 mM MgCl$_2$ and 10 mM NaF. The assay was terminated by the addition of 5 mL of cold Tris-HCl buffer to the tubes and rapid filtration over Whatman GF/C filters using a Brandel cell harvester. The assay was terminated as described above and the filters counted in a gamma counter. The nonspecific binding was calculated as the amount of label not displaced by 20 uM forskolin. The non specific binding was about 20% of the total bound.

6-$^{125}$I-HPP-Fsk bound with high affinity to bovine brain membranes. Analogs of forskolin that are potent at activating adenylate cyclase displaced 6-$^{125}$I-HPP-Fsk from brain membranes while agents that act at the glucose transporter did not displace 6-$^{125}$I-HPP-Fsk from bovine brain membranes (FIG. 4). Therefore, 6-$^{125}$I-HPP-Fsk can be used to specifically measure forskolin binding sites at adenylate cyclase. Previous binding assays for adenylate cyclase utilize the binding of 3H-forskolin which has a specific activity of 30 Cl/mmol. 6-$^{125}$I-HPP-Fsk has a specific activity which is almost 70-fold higher than 3H-forskolin and can be used to measure adenylate cyclase binding sites in very low amounts of tissue. This ligand has been used to measure adenylate cyclase binding sites in a number of peripheral tissues that contain low concentrations of adenylate cyclase.

EXAMPLE 6

Filtration Binding Assay for the Glucose Transporter using Derivative 8 (7$^{125}$I-HPP-Fsk)

Binding of 7-$^{125}$IHPP-Fsk to Membranes—Crude membranes from human red blood cells were incubated for 60 minutes at 20° C. with 20,000 cpm of 7-$^{125}$IHPP-Fsk. Binding equilibrium was reached by 45 minutes and was constant for at least 2 hours (data not shown). The incubations were carried out at 20° C. for 60 minutes in 12×75 glass test tubes in a total volume of 0.4 mL 50 mM Tris-HCl buffer, pH 7.4. The assay was terminated by the addition of 4 mL of cold Tris-HCl buffer to the tubes at rapid filtration over Whatman GF/C filters using a Brandel cell harvester. The assay was terminated as described above and the filters counted in a gamma counter. The nonspecific binding was calculated as the amount of label not displaced by 20 μM forskolin. The non specific binding was about 20% of the total bound.

7-$^{125}$I-HPP-Fsk bound with high affinity (Kd<10 nM) to human erythrocyte membranes. Binding assays were carried out using a filtration binding assay to separate the bound from the free 7-$^{125}$I-HPP-Fsk. The amount of 7-$^{125}$I-HPP-Fsk that bound was linearly proportional to the amount of membrane protein and was displacable with forskolin and derivatives of forskolin. In particular, lipophilic analogs of forskolin were very potent at inhibiting the binding of 7-$^{125}$I-HPP-Fsk to erythrocyte membranes. It has previously been demonstrated that lipophilic derivatives of forskolin have high affinity for the glucose transporter. The 7-aminoethylcarbamyl derivative of forskolin, 3, was about 30-fold more potent than the 6-aminoethylcarbamyl derivative of forskolin, 4, at inhibiting the binding of 7-$^{125}$I-HPP-Fsk to the erythrocyte membranes (FIG. 6). The binding of 7-$^{125}$I-HPP-Fsk was inhibited by D-glucose, forskolin, and cytochlasin B but not by L-glucose (FIGS. 6,7). The ability of other sugar analogs to compete for the binding was consistent with 7-$^{125}$I-HPP-Fsk binding to the human glucose transporter. Lipophilic molecules such as phloridzin were relatively potent at inhibiting the binding of 7-$^{125}$I-HPP-Fsk to the erythrocyte membranes.

EXAMPLE 7

Synthesis of Iodinated Derivatives of Aminoalkylcarbamates 1 mCI of Bolton-Hunter reagent from NEN/Dupont is concentrated to dryness under $N_2$. 20 μL of a solution of the aminoalkylcarbamate (1 mg/mL in $CH_2Cl_2$) is added to the reaction vial and allowed to react at room temperature overnight. It is important to use as little volume as possible for the reaction due to the low concentration of the [125]I-Bolton-Hunter reagent. The reaction is monitored by thin layer chromatography on silica plates with ethyl acetate as developing solvent and visualized by autoradiography. The $^{125}$I-labelled Bolton-Hunter reagent has an RF of 0.9 and the radioactive derivatives (for example 8 or 19, respectively, 6-$^{125}$I-HPP-Fsk and 7-$^{125}$I-HPP-Fsk) have an RF of 0.6. The aminoalkylcarbamates of forskolin do not migrate on silica under these conditions. Thus, it is possible to use an excess of the aminoalkylcarbamate to improve the yield. The reaction is applied to a small silica column (0.9 cm×2 cm) equilibrated with ethyl acetate. Fractions (0.3 mL) are collected and monitored by thin layer chromatography on silica plates followed by autoradiography. The fractions corresponding to the radioactive derivatives are pooled and stored at room temperature in ethyl acetate. The radioactive products are separated completely from the amine precursors using these chromatographic conditions and therefore the labelled compounds are assumed to be carried-free with the specific activity of the [125]I-Bolton Hunter reagent (about 2175 Ci/mmol). The yields for the radioactive products range from 50 to 75% of the starting radioactivity.

What is claimed is:

1. A carbamate derivative of forskolin of the formula:

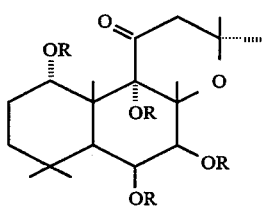

wherein R is $CONH(R_1)NH_2$;

$R_1$ is a hydrocarbon group of the formula $(CH_2)_n$ or $CH_2CH=CH(CH_2)_n$; and
n=1, 2, 4, 5 or 7.

2. A 6-carbamate derivative of forskolin of the formula:

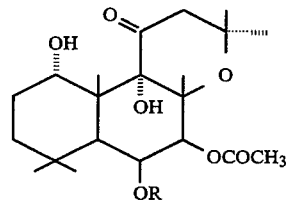

wherein R is $CONH(R_1)NH_2$;
$R_1$ is a hydrocarbon group of the formula $(CH_2)_n$ or $CH_2CH=CH(CH_2)_n$; and
n=1, 2, 4, 5, or 7.

3. A 7carbamate derivative of forskolin of the formula:

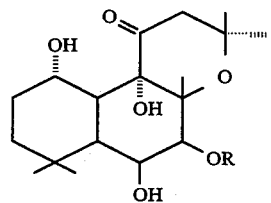

wherein R is $CONH(R_1)NH_2$;
$R_1$ is a hydrocarbon group of the formula $(CH_2)_n$ or $CH_2CH=CH(CH_2)_n$; and
n=1, 2, 4, 5, or 7.

4. A 1-carbamate derivative of forskolin of the formula:

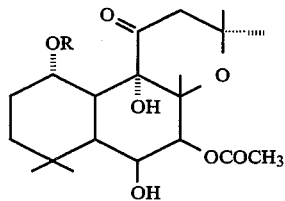

wherein R is $CONH(R_1)NH_2$;
$R_1$ is a hydrocarbon group of the formula $(CH_2)_n$ or $CH_2H=CH(CH_2)_n$; and
n=1, 2, 4, 5, or 7.

5. A 9-carbamate derivative of forskolin of the formula:

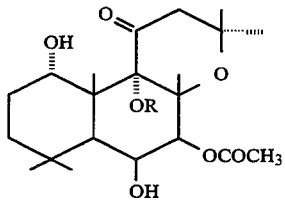

wherein R is $CONH(R_1)NH_2$;
$R_1$ is a hydrocarbon group of the general formula $(CH_2)_n$ or $CH_2CH=CH(CH_2)_n$; and
n=1, 2, 4, 5, or 7.

* * * * *